United States Patent

Furukawa et al.

Patent Number: 6,133,394
Date of Patent: Oct. 17, 2000

[54] METHOD FOR THE PREPARATION OF ORGANOFUNCTIONAL ORGANOPENTASILOXANE, ORGANIC RESIN MODIFIER AND ORGANIC RESINS

[75] Inventors: Haruhiko Furukawa; Tadashi Okawa; Hiroshi Ueki; Yoshitsugu Morita, all of Chiba Prefecture, Japan

[73] Assignee: Dow Corning Toray Silicone Co., Ltd., Tokyo, Japan

[21] Appl. No.: 09/237,280

[22] Filed: Jan. 26, 1999

[30] Foreign Application Priority Data

Jan. 30, 1998 [JP] Japan .................................. 10-034099

[51] Int. Cl.[7] .......................... C08G 77/12; C08G 77/16; C08G 77/26
[52] U.S. Cl. ................................ 528/15; 528/29; 528/31; 528/38; 528/41; 528/196; 528/219
[58] Field of Search .................................. 528/15, 29, 31, 528/38, 41, 219, 33, 196

[56] References Cited

U.S. PATENT DOCUMENTS

| | | | |
|---|---|---|---|
| 5,009,934 | 4/1991 | Wenski et al. | 427/387 |
| 5,041,513 | 8/1991 | Okinoshima et al. | 528/10 |
| 5,252,703 | 10/1993 | Nakajima et al. | 525/423 |

FOREIGN PATENT DOCUMENTS

| | | |
|---|---|---|
| 135 471 | 7/1984 | European Pat. Off. . |
| 472 911 A2 | 7/1991 | European Pat. Off. . |
| 612 785 A2 | 2/1994 | European Pat. Off. . |
| 755 963 A2 | 7/1996 | European Pat. Off. . |
| 3-79626 | 4/1991 | Japan . |

Primary Examiner—Robert Dawson
Assistant Examiner—Kuo-Liang Peng
Attorney, Agent, or Firm—Alex Weitz

[57] ABSTRACT

A method for preparaing of an organofunctional organopentasiloxane which finds utility as a modifier for organic resins is disclosed, said method comprising:

(I) reacting
  (A) a cyclotrisiloxane and
  (B) an $\alpha,\omega$-dihydrogendiorganodisiloxane in the presence of an
  (C) acid catalyst
  to prepare an $\alpha,\omega$-dihydrogendiorganopentasiloxane having the formula $$R_2HSiO(R_2SiO)_3SiHR_2$$

wherein R independently represents a monovalent group free of aliphatic unsaturation selected from hydrocarbon or halogenated hydrocarbon groups; and (II) running an addition reaction in the presence of (D) a hydrosilylation catalyst between said $\alpha,\omega$-dihydrogendiorganopentasiloxane and (E) an organic compound containing a monovalent group selected from epoxy or phenol groups as well as an unsaturated aliphatic hydrocarbon group. In a variation of the method, the $\alpha,\omega$-dihydrogendiorganopentasiloxane is reacted with (F) an organic compound bearing an unsaturated aliphatic hydrocarbon group as well as a monovalent group selected from triorganosilyl-protected amino, triorganosilyl-protected carboxyl, triorganosilyl-protected hydroxyl or triorganosilyl-protected phenol and the protective triorganosilyl groups are subsequently removed.

18 Claims, No Drawings

METHOD FOR THE PREPARATION OF ORGANOFUNCTIONAL ORGANOPENTASILOXANE, ORGANIC RESIN MODIFIER AND ORGANIC RESINS

FIELD OF THE INVENTION

The invention relates to methods for the preparation of organofunctional organopolysiloxane, to organic resin modifiers, and to organic resins. More particularly, the invention relates to methods for the preparation of very pure organofunctional organopentasiloxanes that are functionalized with an amino group, epoxy group, carboxyl group, hydroxyl group, or phenol group at both molecular chain terminals. This invention also relates to organic resin modifiers whose base ingredient is organofunctional organopentasiloxane as afforded by the instant preparative methods and to organic resins as afforded by modification by these organic resin modifiers.

BACKGROUND OF THE INVENTION

Polyorganosiloxanes carrying organofunctional groups find wide use as organic resin modifiers. In particular, Japanese Patent Application Laid Open Number Hei 3-79626 (79,626/1991) and Japanese Patent Application Laid Open Number Hei 4-36321 (36,321/1992) teach that organofunctional group-endblocked polyorganosiloxanes can be copolymerized into polycondensation-type organic resins such as polycarbonate resins and polyimide resins and are extremely useful for modifying the functional properties of such resins. Unfortunately, the organofunctional polyorganosiloxanes used for this application have generally suffered from a low purity since they were prepared by an equilibration polymerization reaction. More specifically, these polyorganosiloxanes contained undesirable admixtures such as high molecular weight polyorganosiloxane and the organofunctional group-free organocyclosiloxane employed as starting material. The use of such a polyorganosiloxane mixture as an organic resin modifier makes it quite difficult to adjust or control molecular weight and prevents the production of organic resin with a constant or specified composition. The resulting organic resin will, in addition, suffer from impaired mechanical properties. The presence of the high molecular weight polyorganosiloxane also impairs heat resistance of the modified organic resin and leads to molding defects due to the conversion of a portion of the siloxane component to decomposition gases during the thermal processing that occurs when the resin is mixed or molded. Other problems have arisen from the admixture of the organofunctional group-free organocyclosiloxane starting material into the organic resin, such as (i) the occurrence of appearance defects in moldings prepared from the organic resin and (ii) the failure to obtain the desired properties due to elimination of the organocyclosiloxane during purification of the organic resin and the corresponding decline in the amount of polyorganosiloxane blended in the organic resin.

SUMMARY OF THE INVENTION

An object of the present invention is to provide methods for preparing very pure organofunctional organopentasiloxane bearing an amino, epoxy, carboxyl, hydroxyl, or phenol group at both molecular chain terminals. Another object of the present invention is to provide an organic resin modifier whose base ingredient is the organofunctional organopentasiloxane afforded by the instant preparative methods. Yet another object of the present invention is to provide organic resins that have been modified by the organic resin modifier according to the present invention.

The invention therefore relates to a method for preparing organofunctional organopentasiloxane having the formula

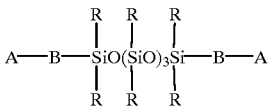

wherein R represents a monovalent hydrocarbon or halogenated hydrocarbon group which is free of aliphatic unsaturation, A is an epoxy or phenol group, and B represents a divalent organic group containing at least 2 carbon atoms, said method being characterized by synthesizing an α,ω-dihydrogenorganopentasiloxane of the formula $R_2HSiO(R_2SiO)_3SiHR_2$ (R is defined as above) by reacting
(A) cyclotrisiloxane of the formula

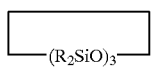

(R is defined as above) and
(B) a disiloxane of the formula $R_2HSiOSiHR_2$ (R is defined as above) in the presence of
(C) an acid catalyst
and then running an addition reaction in the presence of (D) hydrosilylation catalyst between the α,ω-dihydrogenorganopentasiloxane and (E) an organic compound containing an epoxy or phenol group and an unsaturated aliphatic hydrocarbon group.

The invention also relates to a method for preparing organofunctional organopentasiloxane of the formula

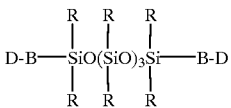

wherein B and R are as defined above and D is a group selected from amino, carboxyl, hydroxyl, or phenol groups, said method being characterized by reacting the above described α,ω-dihydrogenorganopentasiloxane with (F) an organic compound bearing an unsaturated aliphatic hydrocarbon group and a group selected from triorganosilyl-protected amino, triorganosilyl-protected carboxyl, triorganosilyl-protected hydroxyl, or triorganosilyl-protected phenol groups, said reaction taking place in the presence of a hydrosilation catalyst, and subsequently carrying out a reaction that removes the triorganosilyl group.

The invention additionally relates to organic resin modifiers that employ as their base ingredient an organofunctional organopentasiloxane as afforded by the above-described preparative methods.

The invention further relates to organic resins that have been modified by the instant organic resin modifiers.

DETAILED DESCRIPTION OF THE INVENTION

The method for synthesizing the organofunctional organopentasiloxane with the general formula

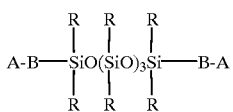

will be explained first. Each R in formula (i) is independently selected from aliphatic unsaturation-free monovalent hydrocarbon or halogenated hydrocarbon groups. These groups can be specifically exemplified by alkyl groups such as methyl, ethyl, propyl, and butyl; aryl groups such as phenyl, tolyl, and xylyl; aralkyl groups such as benzyl and phenethyl; and halogenated hydrocarbon groups such as trifluoropropyl and chloromethylphenethyl. Methyl is preferred for R based on ease of synthesis and economics. The group A is an epoxy or phenol group wherein the epoxy group can be represented by the formulas

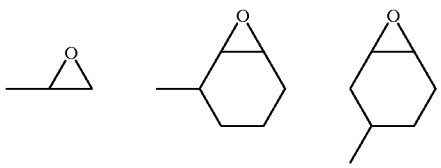

and the phenol group (i.e., a hydroxyphenyl group or a substituted hydroxyphenyl group) can be represented by the formula

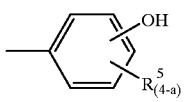

in which $R^5$ is $C_1$ to $C_4$ alkyl or alkoxy or a halogen atom and the subscript a is an integer from 0 to 4. This phenol group can be specifically exemplified by 2-phenol, 4-phenol, and 3-methoxy-4-phenol. The group B of formula (i) is a divalent organic group that contains at least 2 carbon atoms and can be an alkylene group, an alkyleneoxyalkylene group, alkylenepolyoxyalkylene group with the formula —$C_bH_{2b}(OC_cH_{2c})_x$— (b and c are numbers from 2 to 12 and x is a number from 1 to 10), or an carbonyl group. Specific examples of the alkylene group are methylene, ethylene, propylene, butylene, pentylene, hexylene, decylene, dodecylene, and undecylene. Specific examples of the alkyleneoxyalkylene group are methyleneoxypropylene, ethyleneoxyethylene, ethyleneoxypropylene, and propyleneoxypropylene. Specific examples of the alkylenepolyoxyalkylene group are propylenepolyoxyethylene and propylenepolyoxypropylene.

The cyclotrisiloxane (A) used in this preparative method according to the present invention has the formula

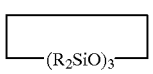

in which R is defined as above. This cyclotrisiloxane can be specifically exemplified by hexamethylcyclotrisiloxane, hexaethylcyclotrisiloxane, 1,3,5-triphenyltrimethylcyclotrisiloxane, and 1,3,5-tris(trifluoropropyl)trimethylcyclotrisiloxane.

The disiloxane (B) used in this preparative method according to the present invention has the formula $$R_2HSiOSiHR_2 \quad (iii)$$

in which R is defined as above. This disiloxane is specifically exemplified by 1,1,3,3-tetramethyldisiloxane, 1,1,3,3-tetraethyldisiloxane, and 1,1,3,3-tetraphenyldisiloxane.

The acid catalyst (C) used in this preparative method according to the present invention can be, for example, a protonic acid such as hydrochloric acid, sulfuric acid, trifluoroacetic acid, or trifluoromethanesulfonic acid, or a Lewis acid such as ferric chloride, aluminum chloride, zinc chloride, or titanium chloride. Strong acids such as hydrochloric acid and perfluoroalkanesulfonic acid are preferred for the purpose of improving the reaction conversion. Trifluoromethanesulfonic acid is particularly preferred. In order to prevent side reactions such as random rearrangement of the siloxane bond and cyclotrisiloxane homopolymerization, these strong acids should be added in trace amounts which are nevertheless sufficient to induce the desired reaction. In specific terms, while this addition will vary as a function of such factors as the acidity of the particular catalyst used and the amount of water or silanol compound in the reaction system, it is preferably no more than 1,000 ppm (parts per million) based on the total weight of components (A) and (B). In the particular case of trifluoromethanesulfonic acid, it will be sufficient to add this catalyst at from 10 to 1,000 ppm based on the total amount of reaction mixture. Since the use of less acid makes possible the use of less basic compound for neutralization of the acid or less water for washing out the acid, these considerations argue for the use of the minimum amount of acid necessary.

The hydrosilylation catalyst (D) used in this preparative method according to the present invention is a catalyst that accelerates the hydrosilylation reaction and can be exemplified by transition metal catalysts such as those of platinum, rhodium, and palladium. Platinum catalysts are preferably used based on their reaction rate and selectivity. The platinum catalyst can be specifically exemplified by chloroplatinic acid, alcohol solutions of chloroplatinic acid, platinum/olefin complexes, platinum/vinyl-functional siloxane complexes, platinum-on-silica, and platinum-on-activated carbon.

The instant preparative method employs (E) an organic compound that bears an epoxy or phenol group as well as an unsaturated aliphatic hydrocarbon group. Compound (E) can be, for example, allyl glycidyl ether, vinylcyclohexene epoxide, or glycidyl methacrylate. The organic compound carrying both a phenol group and an unsaturated aliphatic hydrocarbon group can be, for example, 2-allylphenol, 4-allylphenol, eugenol, or 2-propenylphenol.

The preparative method under consideration commences with the synthesis of an α,ω-dihydrogenorganopentasiloxane of the formula $$R_2HSiO(R_2SiO)_3SiHR_2 \quad (iv)$$

by a nonequilibration reaction of the cyclotrisiloxane (A) and the disiloxane (B) in the presence of the acid catalyst (C), wherein R is as defined above. The molar ratio of the disiloxane (B) the cyclotrisiloxane (A) is preferably from 0.7 to 10.0, more preferably from 0.9 to 5.0, and even more preferably from 0.95 to 2.00. This molar ratio between components (A) and (B) is important for the selective synthesis of the α,ω-dihydrogenorganopentasiloxane. This reaction can be specifically represented by the following equation.

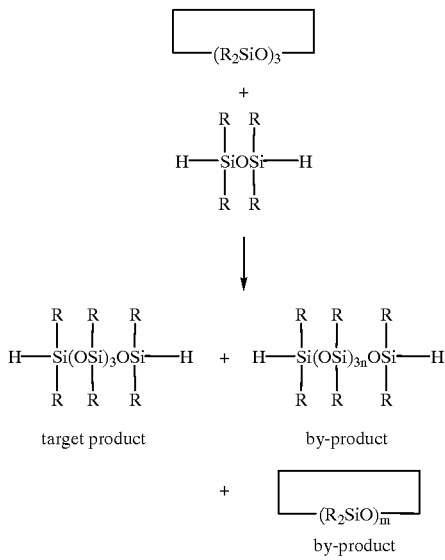

target product    by-product by-product

In the preceding equation, R is defined as above, n is an integer equal to or greater than 2, and m is an integer with a value from 4 to 20. The content of the α,ω-dihydrogenorganopentasiloxane in the reaction mixture afforded by the method of the present invention will be at least 3 times the content of α,ω-dihydrogenorganooctasiloxane $(R_2HSiO(R_2SiO)_6SiHR_2)$ that is the main component in the by-products. It is also possible to diminish the production of the above-described cyclic and chain oligosiloxane by-products by adding water or a silanol compound to the reaction under consideration. Silanol compounds effective in this regard include the various cyclic, chain, and branched monosilanol and polysilanol compounds. Water or silanol compound is preferably added at no more than 1 weight % referred to the total reaction mixture. The rate of the reaction under consideration can be substantially improved by the addition of polar solvent in addition to water or silanol compound. This polar solvent can be a protic solvent as exemplified by alcohols such as methanol, ethanol, and isopropanol and carboxylic acids such as acetic acid, propionic acid, and acrylic acid, or can be an aprotic solvent as exemplified by ethers such as diethyl ether and tetrahydrofuran; ketones such as acetone and methyl ethyl ketone; acetonitrile; dimethylformamide; dimethyl sulfoxide; and hexamethylphosphoric triamide. Two or more of these polar solvents can be used in combination. The amount of polar solvent addition will vary as a function of such factors as the type and amount of addition of the cyclotrisiloxane (A), the disiloxane (B), and the acid catalyst (C), the content of water or silanol compound in the reaction system, and the nature of the polar solvent used. However, as an example, acetonitrile will generally be added at no more than 10 weight % referred to the overall reaction mixture and an acceptable acceleration will generally be seen at an addition no greater than 1 weight %.

The epoxy- or phenol-terminated organofunctional organopentasiloxane of formula (i) is then obtained by running an addition reaction in the presence of the hydrosilylation catalyst (D) between the α,ω-dihydrogenorganopentasiloxane obtained as described above and the organic compound (E) containing an epoxy or phenol group as well as an unsaturated aliphatic hydrocarbon group. This addition reaction must be run by providing at least an equivalent amount of the organic compound (E) with reference to the organopentasiloxane. After completion of the reaction, the excess organic compound can be removed by distillation at reduced pressure. The reaction conditions will vary as a function of the catalyst used, but, taking the use of a platinum catalyst as an example, the reaction is preferably run at 50 to 150° C. for 1 to 6 hours. The subject preparative method according to the present invention can be carried out with or without solvent. Usable solvents are exemplified by aromatic hydrocarbon solvents such as benzene, toluene, and xylene; aliphatic hydrocarbon solvents such as hexane and heptane; ether solvents such as tetrahydrofuran and dimethyl ether; ketone solvents such as acetone and methyl ethyl ketone; ester solvents such as ethyl acetate and butyl acetate; and chlorinated hydrocarbon solvents such as carbon tetrachloride and dichloromethane.

In a variation of the above method, the synthesis of an organofunctional organopentasiloxane of the formula

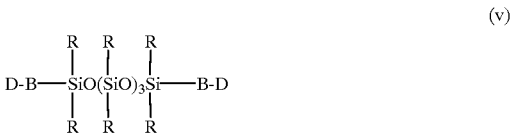

(v)

will now be considered in detail. R and B in formula (v) are the same as defined above while D is a group selected from amino, carboxyl, hydroxyl, or phenol groups.

This second preparative method according to the present invention uses an organic compound (F) containing a triorganosilyl-protected amino group and an unsaturated aliphatic hydrocarbon group, as may be exemplified by allylamine and methallylamine, in each case protected by trimethylsilyl, triethylsilyl, phenyldimethylsilyl, or t-butyldimethylsilyl. Alternatively, organic compound (F) may contain a triorganosilyl-protected carboxyl group and an unsaturated aliphatic hydrocarbon group, as may be exemplified by acrylic acid, methacrylic acid, undecenoic acid, octenoic acid, and decenoic acid, in each case protected by trimethylsilyl, triethylsilyl, phenyldimethylsilyl, or t-butyldimethylsilyl. Organic compound (F) may also contain triorganosilyl-protected hydroxyl and an unsaturated aliphatic hydrocarbon group, as may be exemplified by allyl alcohol, ethylene glycol monoallyl ether, and polyethylene glycol monoallyl ether, in each case protected by trimethylsilyl, triethylsilyl, phenyldimethylsilyl, or t-butyldimethylsilyl. Further, organic compound (F) may contain a triorganosilyl-protected phenol group and an unsaturated aliphatic hydrocarbon group, as may be exemplified by 2-allylphenol, 4-allylphenol, eugenol, and 2-propenylphenol, in each case protected by trimethylsilyl, triethylsilyl, phenyldimethylsilyl, or t-butyldimethylsilyl. The technique for protecting the organofunctional group with the triorganosilyl group is not critical and can be exemplified by reacting hexaorganodisilazane, triorganohalosilane, etc., with an organic compound containing an amino, carboxyl, hydroxyl, or phenol group and an unsaturated aliphatic hydrocarbon group.

The second preparative method also commences with the synthesis of the α,ω-dihydrogenorganopentasiloxane R₂HSiO(R₂SiO)₃SiHR₂ by the nonequilibration reaction of the cyclotrisiloxane (A) and the disiloxane (B) in the presence of the acid catalyst (C), as described above.

The amino-, carboxyl-, hydroxyl- or phenol-terminated organofunctional organopentasiloxane according to formula (v) can be obtained by running an addition reaction in the presence of the hydrosilylation catalyst (D) between the α,ω-dihydrogenorganopentasiloxane of formula (iv) prepared as described above and the organic compound (F) containing an unsaturated aliphatic hydrocarbon group and a triorganosilyl-protected amino, carboxyl, hydroxyl, or phenol group and thereafter running a reaction that removes the triorganosilyl group. This addition reaction must be run by providing at least an equivalent amount of the organic compound (F) with reference to the organopentasiloxane. The reaction conditions will vary as a function of the catalyst used, but, taking the use of a platinum catalyst as an example, the reaction is preferably run at 50 to 150° C. for 1 to 6 hours. The triorganosilyl-elimination reaction that is run after the addition reaction can be carried out by decomposing the protective triorganosilyl group by the addition of water or alcohol. Decomposition by the addition of excess alcohol is preferred based on the ease of reaction and ease of reaction by-product removal. This triorganosilyl-elimination reaction is preferably run using heating and/or a strong acid or strong base catalyst to promote the development of the reaction. After carrying out this triorganosilyl-elimination reaction, the excess organic compound and other by-products will ordinarily be removed by distillation under reduced pressure. The subject preparative method according to the present invention can be carried out with or without solvent. Usable solvents are exemplified by aromatic hydrocarbon solvents such as benzene, toluene, and xylene; aliphatic hydrocarbon solvents such as hexane and heptane; ether solvents such as tetrahydrofuran and dimethyl ether; ketone solvents such as acetone and methyl ethyl ketone; ester solvents such as ethyl acetate and butyl acetate; and chlorinated hydrocarbon solvents such as carbon tetrachloride and dichloromethane.

The preparative methods according to the present invention are characterized by their ability to efficiently produce very pure organofunctional organopentasiloxane that bears at both molecular chain terminals a group selected from amino, epoxy, carboxyl, hydroxyl, or phenol groups. The organofunctional organopentasiloxane under consideration can be exemplified by compounds with the following structures.

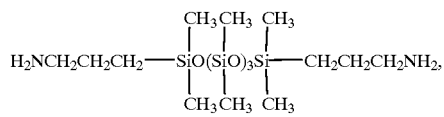

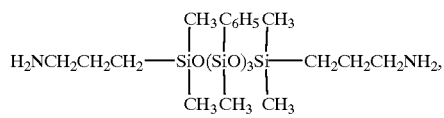

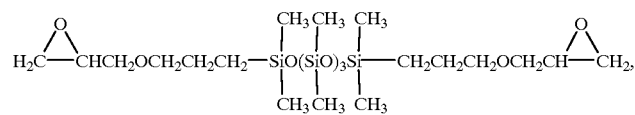

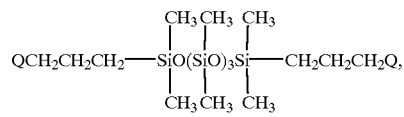

where Q=

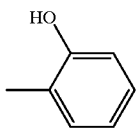

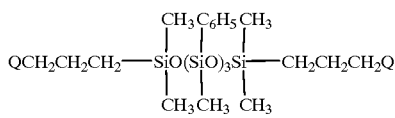

where Q=

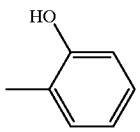

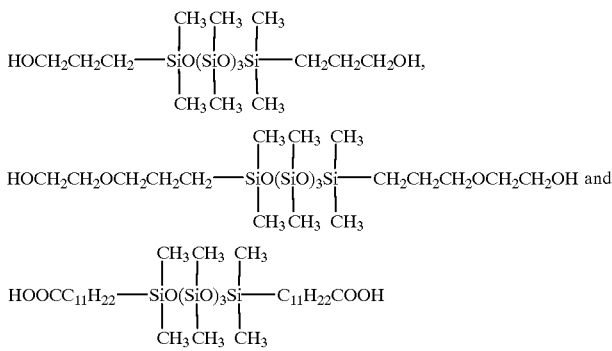

The organofunctional organopentasiloxane afforded by the preparative methods of the present invention are useful as modifiers for a variety of organic resins. The base ingredient of the organic resin modifier according to the present invention is organofunctional organopentasiloxane as afforded by the above-described preparative methods that carries a group selected from amino, epoxy, carboxyl, hydroxyl, or phenol groups at both molecular chain terminals. The organic resin modifier according to the present invention can be used as a modifier of thermoplastic resins such as polyethylene resins, polypropylene resins, polymethyl methacrylate resins, polyvinyl chloride resins, polystyrene resins, high-impact polystyrene resins, ABS resins, AS resins, polyethylene terephthalate resins, polybutylene terephthalate resins, polyamide resins, polyimide resins, polyamideimide resins, and polyacetal resins, and thermosetting resins such as unsaturated polyester resins, acrylic resins, phenolic resins, urea resins, melamine resin, and epoxy resins. For example, by utilizing the reactivity of its amino group, the amino-terminated organofunctional organopentasiloxane can be used as a copolymerization component for polyimide resins, polyamide resins, polyamideimide resins, and polycarbonate resins. The epoxy-terminated organofunctional organopentasiloxane can be utilized as a copolymerization component for epoxy resins; the carboxyl-terminated organofunctional organopentasiloxane can be utilized as a copolymerization component for polyethylene terephthalate resins, polybutylene terephthalate resins, and polyamide resins; the hydroxyl-terminated organofunctional organopentasiloxane can be utilized as a copolymerization component for polyethylene terephthalate resins and polybutylene terephthalate resins; and the phenol-terminated organofunctional organopentasiloxane can be utilized as a copolymerization component for polycarbonate resins.

An advantageous feature of the organic resin modifier according to the present invention is its ability to impart a variety of properties to organic resins, such as release properties, water repellency, surface lubricity, flexibility, and adhesiveness. The organic resin modifier according to the present invention is therefore particularly suitable for application in the various organic resins that are used, for example, in molding materials, paints, and coatings.

Organic resin according to the present invention is an organic resin that has been modified by the above-described organic resin modifier according to the present invention. The amino-, epoxy-, carboxyl-, hydroxyl- or phenol-terminated organofunctional organopentasiloxane that is the base ingredient of this organic resin modifier can react with a variety of organic resin monomers to provide a copolymer in which the siloxane unit has been introduced into the organic resin, or it may simply be blended with the organic resin to give an organic resin composition. There are no particular restrictions on the organic resins applicable for this purpose, and these organic resins can be exemplified by thermoplastic resins such as polyethylene resins, polypropylene resins, polymethyl methacrylate resins, polyvinyl chloride resins, polystyrene resins, high-impact polystyrene resins, ABS resins, AS resins, polyethylene terephthalate resins, polybutylene terephthalate resins, polyamide resins, polyimide resins, polyamideimide resins, and polyacetal resins, and by thermosetting resins such as unsaturated polyester resins, acrylic resins, phenolic resins, urea resins, melamine resins, and epoxy resins. These organic resins may be used individually or as mixtures of two or more selections.

Organic resin according to the present invention can be, for example, polyimide resin comprising 0.1 to 100 mole % structural unit with the general formula

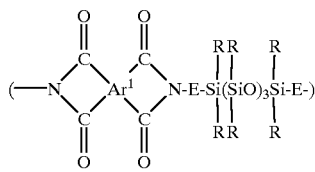

and 99.9 to 0 mole % structural unit with the general formula

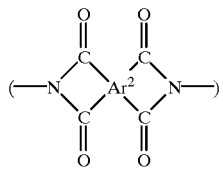

in which $Ar^1$ and $Ar^2$ are tetravalent organic groups containing at least 1 aromatic ring, E is the group $—R^1—$ or $—R^1—NH—R^1—$ ($R^1$ is $C_1$ to $C_{10}$ alkylene), and R is defined as above. This organic resin can also be polycarbonate resin comprising 0.1 to 100 mole % structural unit with the general formula

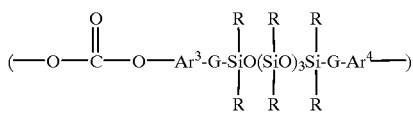

and 99.9 to 0 mole % structural unit with the general formula

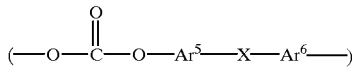

in which $Ar^3$, $Ar^4$, $Ar^5$, and $Ar^6$ represent substituted and unsubstituted aromatic hydrocarbon groups; each G is independently selected from $C_1$ to $C_{10}$ divalent alkylene or alkyleneoxyalkylene groups; X is a group selected from a single bond, $—O—$, $—CO—$, $—S—$, $—SO—$, $—SO_2—$, $—CR^2R^3—$ ($R^2$ and $R^3$ are selected from the hydrogen atom, $C_1$ to $C_{10}$ substituted and unsubstituted alkyl groups, or $C_6$ to $C_{12}$ substituted or unsubstituted aryl groups), $C_5$ to $C_{11}$ substituted or unsubstituted cycloalkylidene groups, $C_2$ to $C_{12}$ substituted or unsubstituted alkylene groups, 9,9-fluorenylidene, substituted or unsubstituted pyrazylidene groups, or $C_6$ to $C_{24}$ substituted or unsubstituted arylene groups; and R is defined as above.

The organic resin according to the present invention may also be mixed with reinforcing filler and various additives. The reinforcing filler is exemplified by glass fiber, carbon fiber, glass fabric, calcium carbonate, mica, and talc. The various additives can be, for example, antioxidants, plasticizers, lubricants, antistatic agents, flame retardants, and colorants such as pigments and dyes.

An advantageous feature of organic resin according to the present invention is that it can exhibit a variety of highly desirable properties, such as release properties, water repellency, surface lubricity, flexibility, and adhesiveness.

EXAMPLES

The invention is explained in greater detail below through working examples.

Synthesis Example 1

Twenty grams (0.090 mole) of hexamethylcyclotrisiloxane, 13.3 g (0.099 mole) tetramethyldisiloxane, 24 μL water, and 0.9 g acetonitrile were introduced into a four-neck flask equipped with a reflux condenser, thermometer, and stirrer. 1.5 μL trifluoromethanesulfonic acid was then introduced into this mixture and it was stirred for 9 hours at room temperature. After neutralization by blowing in ammonia, filtration yielded a colorless and transparent liquid. Analysis of this liquid by NMR spectroscopy confirmed it to be α,ω-dihydrogendimethylpentasiloxane with the following structural formula.

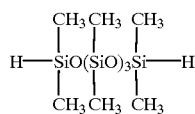

This α,ω-dihydrogendimethylpentasiloxane had a purity of 97%.

Example 1

While operating under a nitrogen current, 30.4 g (0.266 mole) of allyl glycidyl ether and sufficient platinum/tetramethyldivinyldisiloxane complex to provide 0.0013 g platinum metal were introduced into a four-neck flask equipped with a reflux condenser, thermometer, and stirrer. This was then heated to approximately 80° C., and 39.6 g (0.111 mole) of the α,ω-dihydrogendimethylpentasiloxane afforded by Synthesis Example 1 was added dropwise over a period of approximately two hours. After the completion of addition, the solution was stirred for approximately four hours while heating at approximately 100° C. The infrared absorption spectrum was measured on a sample taken at this point, and the disappearance from this spectrum of the characteristic absorption for the SiH group around 2100 cm$^{-1}$ confirmed that the reaction had gone to completion. 60 g of a clear, yellowish-brown liquid was obtained by removal of the low boilers under reduced pressure. Analysis of the obtained liquid by gel permeation chromatography and NMR spectroscopy confirmed it to be the organofunctional organopentasiloxane (hereafter designated as organofunctional organopentasiloxane 1) with the following structural formula.

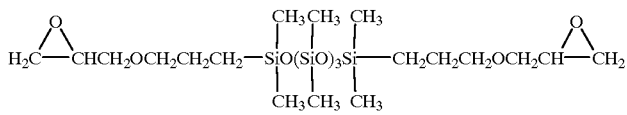

Organofunctional organopentasiloxane 1 had a purity of 96%.

Example 2

While operating under a nitrogen current, 33.2 g (0.247 mole) of allylphenol and sufficient platinum/tetramethyldivinyldisiloxane complex to provide 0.0013 g platinum metal were introduced into a four-neck flask equipped with a reflux condenser, thermometer, and stirrer. This was then heated to approximately 80° C., and 36.8 g (0.103 mole) of the α,ω-dihydrogendimethylpentasiloxane afforded by Synthesis Example 1 was added dropwise over a period of approximately two hours. After the completion of addition, the solution was stirred for approximately four hours while heating at approximately 100° C. The infrared absorption spectrum was measured on a sample taken at this point, and the disappearance from this spectrum of the characteristic absorption for the SiH group around 2100 cm$^{-1}$ confirmed that the reaction had gone to completion. 59 g of a clear, yellowish-brown liquid was obtained by removal of the low boilers under reduced pressure. Analysis of the obtained liquid by gel permeation chromatography and NMR spectroscopy confirmed it to be the organofunctional organopentasiloxane (hereafter designated as organofunctional organopentasiloxane 2) with the following structural formula.

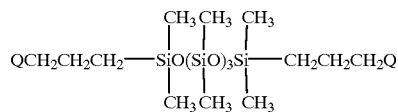

where Q=

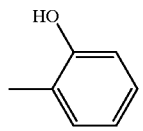

Organofunctional organopentasiloxane 2 had a purity of 96%.

Example 3

While operating under a nitrogen current, 37.2 g (0.288 mole) of trimethylsilylated allylamine and sufficient platinum/tetramethyldivinyldisiloxane complex to provide 0.0012 g platinum metal were introduced into a four-neck flask equipped with a reflux condenser, thermometer, and stirrer. This was then heated to approximately 80° C., and 42.8 g (0.120 mole) of the α,ω-dihydrogendimethylpentasiloxane afforded by Synthesis Example 1 was added dropwise over a period of approximately two hours. After the completion of addition, the reaction was stirred for approximately 4 hours at approximately 120° C. The infrared absorption spectrum was measured on a sample taken at this point, and the disappearance from this spectrum of the characteristic absorption for the SiH group around 2100 cm$^{-1}$ confirmed that the reaction had gone to completion. 28.0 g (0.875 mole) methanol was then added to the reaction solution with stirring for one hour while heating at approximately 70° C. 52 g of a clear, yellowish-brown liquid was subsequently obtained by removal of the low boilers under reduced pressure. Analysis of the obtained liquid by gel permeation chromatography and NMR spectroscopy confirmed it to be the organofunctional organopentasiloxane (hereafter designated as organofunctional organopentasiloxane 3) with the following structural formula.

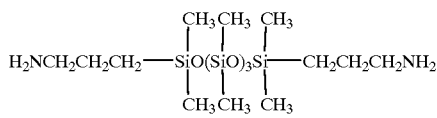

Organofunctional organopentasiloxane 3 had a purity of 96%.

Example 4

While operating under a nitrogen current, 43.1 g (0.168 mole) of trimethylsilylated undecylenic acid and sufficient platinum/tetramethyldivinyldisiloxane complex to provide 0.0010 g platinum metal were introduced into a four-neck flask equipped with a reflux condenser, thermometer, and stirrer. This was then heated to approximately 80° C., and 25.0 g (0.070 mole) of the α,ω-dihydrogendimethylpentasiloxane afforded by Synthesis Example 1 was added dropwise over a period of approximately two hours. Stirring was continued after the completion of addition for five hours while heating at 100° C. The infrared absorption spectrum was measured on a sample taken at this point, and the disappearance from this spectrum of the characteristic absorption for the SiH group around 2100 cm$^{-1}$ confirmed that the reaction had gone to completion. 16.1 g (0.503 mole) methanol was then added to the reaction solution with stirring for three hours while heating at 50° C. 50 g of a clear, yellowish-brown liquid was subsequently obtained by removal of the low boilers under reduced pressure. Analysis of the obtained liquid by NMR spectroscopy and measurement of its molecular weight distribution by GPC confirmed it to be the organofunctional organopentasiloxane (hereafter designated as organofunctional organopentasiloxane 4) with the following structural formula.

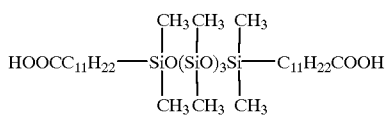

Organofunctional organopentasiloxane 4 had a purity of 94%.

Example 5

While operating under a nitrogen current, 31.3 g (0.240 mole) of trimethylsilylated allyl alcohol and sufficient platinum/tetramethyldivinyldisiloxane complex to provide 0.0012 g platinum metal were introduced into a four-neck flask equipped with a reflux condenser, thermometer, and stirrer. This was then heated to approximately 80° C., and 35.7 g (0.100 mole) of the α,ω-dihydrogendimethylpentasiloxane afforded by Synthesis Example 1 was added dropwise over a period of approximately two hours. Stirring was continued after the completion of addition for five hours while heating at 100° C. The infrared absorption spectrum was measured on a sample taken at this point, and the disappearance from this spectrum of the characteristic absorption for the SiH group around 2100 cm$^{-1}$ confirmed that the reaction had gone to completion. 23.0 g (0.719 mole) methanol and 2 g acetic acid were then added to the reaction solution with stirring for approximately one hour while heating at approximately 50° C. 42 g of a clear, yellowish-brown liquid was subsequently obtained by removal of the low boilers under reduced pressure. Analysis of the obtained liquid by gel permeation chromatography and NMR spectroscopy confirmed it to be the organofunctional organopentasiloxane (hereafter designated as organofunctional organopentasiloxane 5) with the following structural formula.

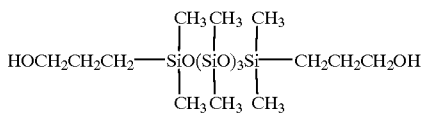

Organofunctional organopentasiloxane 5 had a purity of 96%.

Example 6

While operating under a nitrogen current, 51.0 g (0.247 mole) of trimethylsilylated allylphenol and sufficient platinum/tetramethyldivinyldisiloxane complex to provide 0.0013 g platinum metal were introduced into a four-neck flask equipped with a reflux condenser, thermometer, and stirrer. This was then heated to approximately 80° C., and 36.8 g (0.103 mole) of the α,ω-dihydrogendimethylpentasiloxane afforded by Synthesis Example 1 was added dropwise over a period of approximately two hours. Stirring was continued after the completion of addition for approximately 4 hours while heating at approximately 100° C. The infrared absorption spectrum was measured on a sample taken at this point, and the disappearance from this spectrum of the characteristic absorption for the SiH group around 2100 cm$^{-1}$ confirmed that the reaction had gone to completion. 23.7 g (0.741 mole) methanol and 2 g acetic acid were then added to the reaction solution with stirring for approximately one hour while heating at approximately 50° C. 57 g of a clear, yellowish-brown liquid was subsequently obtained by removal of the low boilers under reduced pressure. Analysis of the obtained liquid by gel permeation chromatography and NMR spectroscopy confirmed it to be the organofunctional organopentasiloxane (hereafter designated as organofunctional organopentasiloxane 6) with the following structural formula.

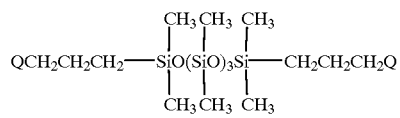

where Q=

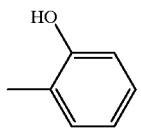

Organofunctional organopentasiloxane 6 had a purity of 96%.

Example 7

While operating under a nitrogen current, 16.11 g of 3,3',4,4'-benzophenonetetracarboxylic dianhydride was introduced into a 500-mL four-neck flask equipped with a stirrer, addition funnel, and thermometer and was dissolved by adding 120 g dry N-methylpyrrolidone. 3.71 g of the dried organofunctional organopentasiloxane 3 afforded by Example 3 was then added dropwise at room temperature. Stirring was continued for 1 hour at room temperature after the completion of addition. 17.29 g 2,2-bis(2-diaminophenoxyphenyl)propane dissolved in 80 g dry N-methylpyrrolidone was then slowly added dropwise while cooling with ice. After the completion of addition, stirring for 1 hour while cooling with ice and then for 4 hours at room temperature yielded the N-methylpyrrolidone solution of a silicone-containing polyamic acid comprising the structural units with the following structural formulas (a) and (b).

Structural Formula (A)

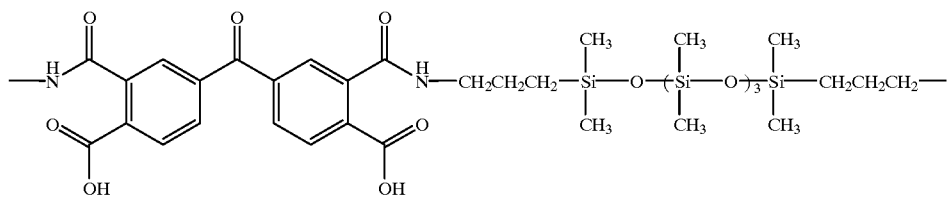

Structural Formula (B)

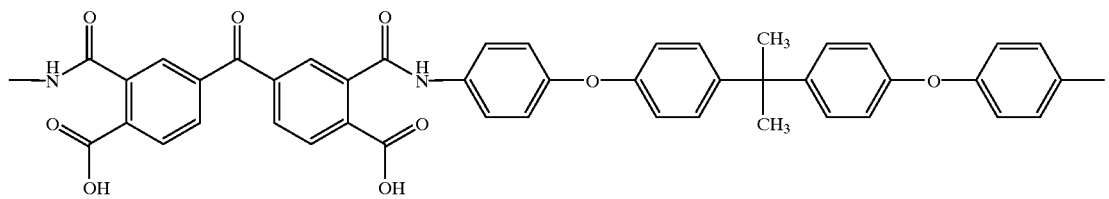

The structural unit (a):structural unit (b) copolymerization ratio (mole %) was 16:84. Measurement of the intrinsic viscosity of the obtained silicone-containing polyamic acid in its N-methylpyrrolidone solution gave a value of 0.46 dL/g.

A film was produced by coating the N-methylpyrrolidone solution of silicone-containing polyamic acid obtained as described above on a Teflon™ plate and gradually heating from 100 to 180° C. under a nitrogen current. This film was peeled from the Teflon™ plate and transferred to a glass support block. It was then gradually heated from 200 to 300° C. under a nitrogen current to give the film of a silicone-containing polyimide resin comprising the structural units with the following structural formulas (1) and (2).

Structural Formula (1)

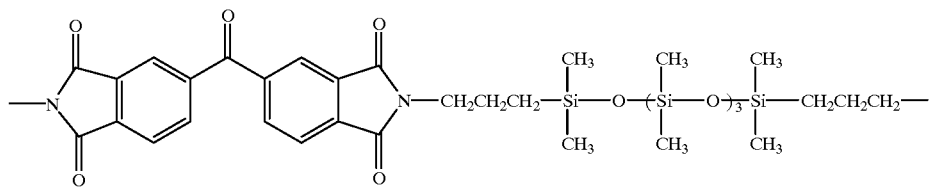

Structural Formula (2)

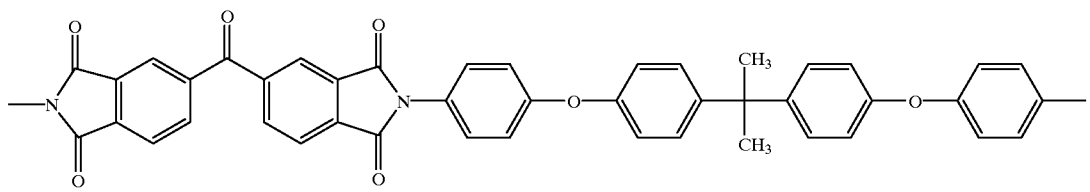

The structural unit (1):structural unit (2) copolymerization ratio (molar ratio) was 16:84.

The appearance of the obtained silicone-containing polyimide resin film was inspected both visually and with an optical microscope, and the contact angle versus water was measured using a contact angle meter. The silicone-containing polyimide resin film was also inserted between two sheets of iron and hot-pressed at from 300 to 350° C. using a heated press to produce an adhesion specimen. The adhesive strength was then measured using a tensile tester by peeling this adhesion specimen apart. In addition, the tensile strength was measured on ten sheets of the film using a tensile tester and the scatter in the measured values was calculated. For the present purposes, a rating of "scatter absent" was assigned when the coefficient of variation (100×standard deviation/average) in the measured values was ≦95%, while a rating of "scatter present" was assigned when the degree of dispersion in the measured values was more than 95%. These results are reported in Table 1.

Example 8

Forty grams of sodium hydroxide were dissolved in 1,370 mL water followed by the dissolution therein while maintaining a temperature of 20° C. of 214.5 g 2,2-bis(4-hydroxyphenyl)propane, 37.8 g organofunctional organopentasiloxane 2 as afforded by Example 2, and 0.46 g hydrosulfite. 910 mL of methylene chloride were added and, while stirring, 4.51 g p-tert-butylphenol were added and 108.8 g phosgene was then blown in over a 60 minute period. After the completion of phosgene injection, the reaction solvent was emulsified by vigorous stirring, 0.46 g triethylamine was added, and polymerization was run while continuing to stir for approximately 1 hour. The resulting polymer solution was separated into aqueous and organic phases, and the organic phase was preliminarily neutralized with phosphoric acid and then repeatedly washed with water until the pH of the wash water became neutral. The addition of a large excess of isopropyl alcohol to the organic phase resulted in the precipitation of the polymer afforded by the reaction. This precipitate was filtered off and dried to give 250 g of a white powder. Analysis of this white powder by $C^{13}$-NMR spectroscopy and $Si^{29}$-NMR spectroscopy confirmed it to be a silicone-containing polycarbonate resin composed of 6 mole % unit with structural formula (3) and 94 mole % unit with structural formula (4).

Structural Formula (3)

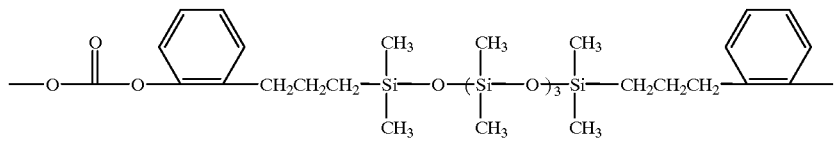

Structural Formula (4)

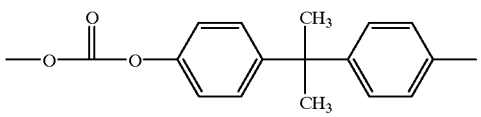

The silicone-containing polycarbonate resin powder obtained as described above was dried at 120° C. for 4 hours and tensile test specimens were prepared from the dry powder by molding with an injection molder. The contact angle versus water and the scatter in tensile strength values were measured on these tensile test specimens as in Example 7. These results are reported in Table 2.

Example 9

Forty grams of sodium hydroxide were dissolved in 1,370 mL water followed by the dissolution therein while maintaining a temperature of 20° C. of 214.5 g 2,2-bis(4-hydroxyphenyl)propane, 37.8 g organofunctional organopentasiloxane 6 as afforded by Example 6, and 0.46 g hydrosulfite. 910 mL of methylene chloride were added and, while stirring, 4.51 g p-tert-butylphenol were added and 108.8 g phosgene was then blown in over a 60 minute period. After the completion of phosgene injection, the reaction solvent was emulsified by vigorous stirring, 0.46 g triethylamine was added, and polymerization was run while continuing to stir for approximately 1 hour. The resulting polymer solution was separated into aqueous and organic phases, and the organic phase was preliminarily neutralized with phosphoric acid and then repeatedly washed with water until the pH of the wash water became neutral. The addition of a large excess of isopropyl alcohol to the organic phase resulted in the precipitation of the polymer afforded by the reaction. This precipitate was filtered off and dried to give 245 g of a white powder. Analysis of this white powder by $C^{13}$-NMR spectroscopy and $Si^{29}$-NMR spectroscopy confirmed it to be a silicone-containing polycarbonate resin composed of 6 mole % unit with structural formula (3) and 94 mole % unit with structural formula (4).

Structural Formula (3)

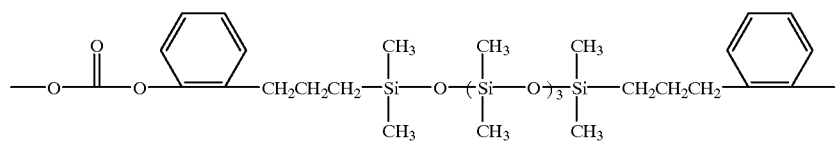

Structural Formula (4)

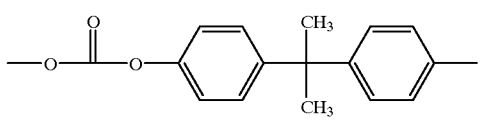

The silicone-containing polycarbonate resin powder obtained as described above was dried at 120° C. for 4 hours and tensile test specimens were prepared from the dry powder by molding with an injection molder. The contact angle versus water and the scatter in tensile strength values were measured on these tensile test specimens as in Example 7. These results are reported in Table 2.

Comparative Example 1

While operating under a nitrogen current, 37.6 g (0.28 mole) of tetramethyldisiloxane, 62.4 g (0.21 mole) octamethylcyclotetrasiloxane, and sufficient trifluoromethanesulfonic acid to provide 1,000 ppm were introduced into a four-neck flask equipped with a reflux condenser, thermometer, and stirrer and stirred while heating at 60° C. for 8 hours. After the completion of stirring, 94 g of a colorless and transparent liquid was obtained by neutralization by blowing in ammonia and filtration. Analysis of this liquid by NMR spectroscopy confirmed it to be a mixture of organosiloxanes with the following formulas.

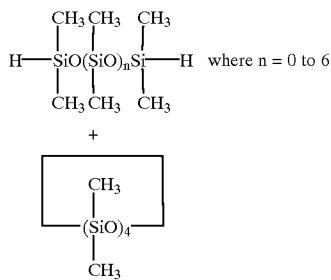

The content of α,ω-dihydrogendimethylpentasiloxane (i.e., n=3) in this mixture as measured by gas chromatography was 15%.

Next, while operating under a nitrogen current, 30.4 g (0.266 mole) allyl glycidyl ether and sufficient platinum/tetramethyldivinyldisiloxane complex to provide 0.0013 g platinum metal were introduced into a four-neck flask equipped with a reflux condenser, thermometer, and stirrer. This was then heated to approximately 80° C., and 39.6 g (0.111 mole) of the organosiloxane mixture obtained as described above was added dropwise over a period of approximately two hours. After the completion of addition, the solution was stirred for approximately four hours while heating at approximately 100° C. The infrared absorption spectrum was measured on a sample taken at this point, and the disappearance from this spectrum of the characteristic absorption for the SiH group around 2100 cm$^{-1}$ confirmed that the reaction had gone to completion. 60 g of a clear, yellowish-brown liquid was subsequently obtained by removal of the low boilers under reduced pressure. Analysis of the obtained liquid by NMR spectroscopy confirmed it to be a mixture of organofunctional organosiloxanes that contained 15% organofunctional organopentasiloxane 1 with the following formula.

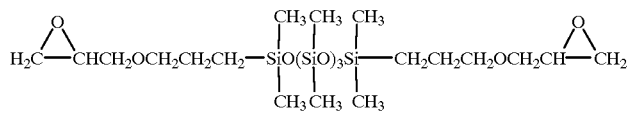

Comparative Example 2

While operating under a nitrogen current, 33.22 g (0.248 mole) allylphenol and sufficient platinum/tetramethyldivinyldisiloxane complex to provide 0.0013 g platinum metal were introduced into a four-neck flask equipped with a reflux condenser, thermometer, and stirrer. This was heated to approximately 80° C. and 36.78 g (0.103 mole) of the organosiloxane mixture obtained in Comparative Example 1 (content of α,ω-dihydrogendimethylpentasiloxane=15%) was added dropwise over a period of approximately two hours. After the completion of addition, the solution was stirred for approximately four hours while heating at approximately 100° C. The infrared absorption spectrum was measured on a sample taken at this point, and the disappearance from this spectrum of the characteristic absorption for the SiH group around 2100 cm$^{-1}$ confirmed that the reaction had gone to completion. 59 g of a clear, light yellow liquid was subsequently obtained by removal of the low boilers under reduced pressure. Analysis of the obtained liquid by NMR spectroscopy confirmed it to be a mixture of organofunctional organosiloxanes that contained 15% organofunctional organopentasiloxane 2 with the following formula.

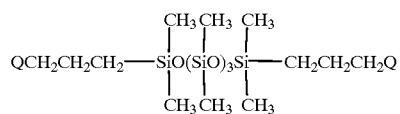

where Q=

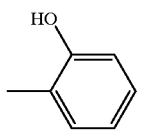

Comparative Example 3

While operating under a nitrogen current, 37.28 g (0.150 mole) 1,3-bis(3-aminopropyl)tetramethyldisiloxane, 33.38 g (0.113 mole) octamethylcyclotetrasiloxane, and sufficient potassium hydroxide to provide 300 ppm were introduced into a four-neck flask equipped with reflux condenser, thermometer, and stirrer and stirred for six hours at 140° C. After neutralization by the addition of acetic acid, 67 g of a clear, light yellow liquid was obtained by filtration. Analysis of the obtained liquid by NMR spectroscopy confirmed it to be a mixture of organofunctional organosiloxanes that contained 8% organofunctional organopentasiloxane 3 with the following formula.

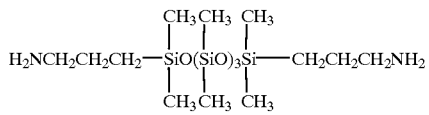

Comparative Example 4

While operating under a nitrogen current, 43.1 g (0.168 mole) trimethylsilylated undecylenic acid and sufficient platinum/tetramethyldivinyldisiloxane complex to provide 0.0012 g platinum metal were introduced into a four-neck flask equipped with a reflux condenser, thermometer, and stirrer. This was heated to approximately 80° C. and 24.98 g (0.070 mole) of the organosiloxane mixture obtained in Comparative Example 1 ($\alpha,\omega$-dihydrogendimethylpentasiloxane content=15%) was added dropwise over a period of approximately two hours. After the completion of addition, the solution was stirred for five hours while heating at 100° C. The infrared absorption spectrum was measured on a sample taken at this point, and the disappearance from this spectrum of the characteristic absorption for the SiH group around 2100 cm$^{-1}$ confirmed that the reaction had gone to completion. 16.1 g (0.503 mole) methanol was then added to the reaction solution with stirring for 3 hours while heating at 50° C. 50 g of a clear, yellowish-brown liquid was subsequently obtained by removal of the low boilers under reduced pressure. Analysis of the obtained liquid by NMR spectroscopy confirmed it to be a mixture of organofunctional organosiloxanes that contained 14% organofunctional organopentasiloxane 4 with the following formula.

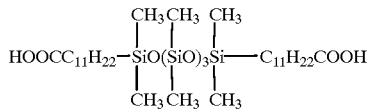

Comparative Example 5

While operating under a nitrogen current, 31.3 g (0.240 mole) trimethylsilylated allyl alcohol and sufficient platinum/tetramethyldivinyldisiloxane complex to provide 0.0012 g platinum metal were introduced into a four-neck flask equipped with a reflux condenser, thermometer, and stirrer. This was heated to approximately 80° C. and 35.7 g (0.100 mole) of the organosiloxane mixture obtained in Comparative Example 1 ($\alpha,\omega$-dihydrogendimethylpentasiloxane content=15%) was added dropwise over a period of approximately two hours. After the completion of addition, the solution was stirred for five hours while heating at 100° C. The infrared absorption spectrum was measured on a sample taken at this point, and the disappearance from this spectrum of the characteristic absorption for the SiH group around 2100 cm$^{-1}$ confirmed that the reaction had gone to completion. 23.0 g (0.719 mole) methanol and 2 g acetic acid were then added to the reaction solution with stirring for approximately 1 hour while heating at approximately 50° C. 42 g of a clear, light yellow liquid was subsequently obtained by removal of the low boilers under reduced pressure. Analysis of the obtained liquid by NMR spectroscopy confirmed it to be a mixture of organofunctional organosiloxanes that contained 15% organofunctional organopentasiloxane 5 with the following formula.

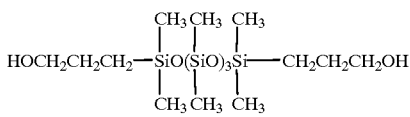

Comparative Example 6

An N-methylpyrrolidone solution of silicone-containing polyamic acid was prepared as in Example 7, but in this case using the mixture of organofunctional organosiloxanes prepared in Comparative Example 3 in place of the organofunctional organopentasiloxane 3 synthesized in Example 3. A film was prepared by coating this N-methylpyrrolidone solution of silicone-containing polyamic acid on a Teflon™ plate and gradually heating from 100 to 180° C. under a nitrogen current. This film was peeled from the Teflon™ plate and transferred to a glass support block. It was then gradually heated from 200 to 300° C. under a nitrogen current to give the film of a silicone-containing polyimide resin. The appearance, contact angle versus water, adhesive strength, and scatter in tensile strength values of the silicone-containing polyimide resin film thus obtained were measured as in Example 7, and the results are reported in Table 1.

Comparative Example 7

230 g white, silicone-containing polycarbonate resin powder was prepared as in Example 8, but in this case using the mixture of organofunctional organosiloxanes prepared in Comparative Example 2 in place of the organofunctional organopentasiloxane 2 synthesized in Example 2. The silicone-containing polycarbonate resin powder thus obtained was dried at 120° C. for 4 hours, after which molded tensile test specimens were fabricated by molding with an injection molder. The contact angle versus water and the scatter in tensile strength values were measured on these molded specimens as in Example 8, and the results are reported in Table 2.

TABLE 1

|  | appearance | contact angle (degrees) | adhesive strength kg/mm$^2$ | scatter in tensile strength values |
|---|---|---|---|---|
| Example 7 | voids not present | 105 | 100 | scatter absent |
| Comparative Example 6 | voids present | 105 | 80 | scatter present |

TABLE 2

| | contact angle (degrees) | scatter in tensile strength values |
|---|---|---|
| Example 8 | 105 | scatter absent |
| Example 9 | 105 | scatter absent |
| Comparative Example 7 | 104 | scatter present |

That which is claimed is:

1. A method for preparing an organofunctional organopentasiloxane having the formula

said method comprising:
(I) reacting
   (A) a cyclotrisiloxane having the formula

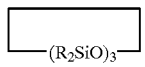 and (B) a disiloxane having the formula $R_2HSiOSiHR_2$ in the presence of an
   (C) acid catalyst
to prepare an α,ω-dihydrogenorganopentasiloxane having the formula $R_2HSiO(R_2SiO)_3SiHR_2$ wherein R independently represents a monovalent group free of aliphatic unsaturation selected from the group consisting of hydrocarbon groups and halogenated hydrocarbon groups, A is selected from the group consisting of epoxy and phenol groups, and B represents a divalent organic group having at least 2 carbon atoms; and (II) running an addition reaction in the presence of (D) a hydrosilylation catalyst between said α,ω-dihydrogenorganopentasiloxane and (E) an organic compound containing a monovalent group selected from the group consisting of epoxy and phenol as well as an unsaturated aliphatic hydrocarbon group.

2. A method for preparing an organofunctional organopentasiloxane having the formula

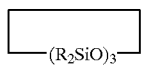 and said method comprising:
(I) reacting
   (A) a cyclotrisiloxane having the formula

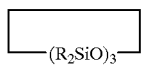 and (B) a disiloxane having the formula $R_2HSiOSiHR_2$ in the presence of an
   (C) acid catalyst
to prepare an α,ω-dihydrogenorganopentasiloxane having the formula $R_2HSiO(R_2SiO)_3SiHR_2$ wherein R independently represents a monovalent group free of aliphatic unsaturation selected from the group consisting of hydrocarbon groups and halogenated hydrocarbon groups, D is selected from the group consisting of amino, carboxyl, hydroxyl, and phenol groups and B represents a divalent organic group having at least 2 carbon atoms;

(II) running an addition reaction in the presence of (D) a hydrosilylation catalyst between said α,ω-dihydrogenorganopentasiloxane and (F) an organic compound bearing an unsaturated aliphatic hydrocarbon group as well as a monovalent group selected from the group consisting of triorganosilyl-protected amino, triorganosilyl-protected carboxyl, triorganosilyl-protected hydroxyl, and triorganosilyl-protected phenol; and (III) carrying out a reaction that removes the triorganosilyl group.

3. The method according to claim 1, wherein each R group is methyl.

4. The method according to claim 2, wherein each R group is methyl.

5. The method according to claim 3, wherein A is selected from the group consisting of

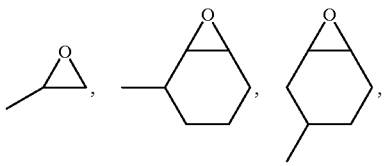

and

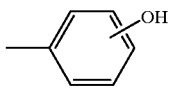

6. An organofunctional organopentasiloxane prepared according to the method of claim 1.

7. An organofunctional organopentasiloxane prepared according to the method of claim 2.

8. The organofunctional organopentasiloxane according to claim 6, wherein each R group is methyl.

9. The organofunctional organopentasiloxane according to claim 7, wherein each R group is methyl.

10. The organofunctional organopentasiloxane according to claim 8, wherein A is selected from the group consisting of

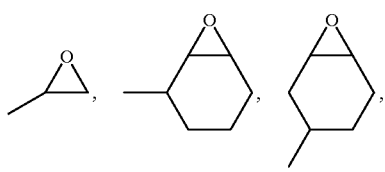

and

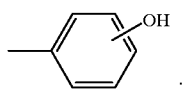

11. An organic resin modified with the organofunctional organopentasiloxane according to claim 6.

12. An organic resin modified with the organofunctional organopentasiloxane according to claim 7.

13. An organic resin modified with the organofunctional organopentasiloxane according to claim 8.

14. An organic resin modified with the organofunctional organopentasiloxane according to claim 9.

15. An organic resin modified with the organofunctional organopentasiloxane according to claim 10.

16. A polycarbonate resin modified with the organofunctional organopentasiloxane according to claim 6.

17. A polycarbonate resin modified with the organofunctional organopentasiloxane according to claim 7.

18. A polyimide resin modified with the organofunctional organopentasiloxane according to claim 7.

* * * * *